(12) United States Patent
Moreland et al.

(10) Patent No.: US 7,985,599 B2
(45) Date of Patent: Jul. 26, 2011

(54) MICROFLUIDIC PLATFORM OF ARRAYED SWITCHABLE SPIN-VALVE ELEMENTS FOR HIGH-THROUGHPUT SORTING AND MANIPULATION OF MAGNETIC PARTICLES AND BIOMOLECULES

(75) Inventors: John Moreland, Louisville, CO (US); Elizabeth Mirowski, Boulder, CO (US); Stephen E. Russek, Louisville, CO (US)

(73) Assignee: The United States of America as represented by the Secretary of Commerce, The National Institute of Standards and Technology, Washington, DC (US)

( * ) Notice: Subject to any disclaimer, the term of this patent is extended or adjusted under 35 U.S.C. 154(b) by 704 days.

(21) Appl. No.: 11/705,889

(22) Filed: Feb. 13, 2007

(65) Prior Publication Data

US 2007/0141728 A1   Jun. 21, 2007

Related U.S. Application Data

(62) Division of application No. 11/061,461, filed on Feb. 18, 2005.

(51) Int. Cl.
*G01N 33/00* (2006.01)
*G01N 33/553* (2006.01)

(52) U.S. Cl. .................... 436/526; 435/4; 435/5; 435/6; 435/7.1; 435/7.2; 435/287.2; 435/287.3; 435/288.3; 435/288.5; 422/68.1; 422/103; 422/104; 360/324; 360/324.1; 360/324.11; 360/324.12

(58) Field of Classification Search .................. None
See application file for complete search history.

(56) References Cited

U.S. PATENT DOCUMENTS

| | | | |
|---|---|---|---|
| 4,843,316 | A | 6/1989 | Hesterman |
| 5,434,826 | A | 7/1995 | Ravipati et al. |
| 5,478,527 | A | 12/1995 | Gustafson et al. |
| 5,793,279 | A | 8/1998 | Nepela |
| 6,175,476 | B1 | 1/2001 | Huai et al. |
| 6,775,110 | B1 | 8/2004 | Hayashi et al. |
| 2002/0024778 | A1 | 2/2002 | Xue et al. |
| 2002/0081714 | A1 | 6/2002 | Jain et al. |
| 2002/0086443 | A1* | 7/2002 | Bamdad .................. 436/526 |

(Continued)

OTHER PUBLICATIONS

Grollier et al., "Switching the magnetic configuration of a spin valve by current induced domain wall motion", Journal of Applied Physics, Oct. 15, 2002, vol. 92, pp. 4825-4827.*

(Continued)

*Primary Examiner* — Unsu Jung
(74) *Attorney, Agent, or Firm* — Butzel Long

(57) ABSTRACT

Arrays of spin-valve elements that can be selectively activated to trap, hold, manipulate and release magnetically tagged biological and chemical particles, including molecules and polymers. The spin-valve elements that can be selectively activated and deactivated by applying a momentary applied magnetic field thereto. The spin valve element array can be used for selectively sorting and transporting magnetic particles one particle at a time within the array. As the magnetically tagged particles are held by the spin-valve elements, application of an auxiliary magnetic field can be used to apply tension or torsion to the held particles or to move, e.g. rotate, the trapped particles. The arrays of spin-valve elements can be used in a variety of applications including drug screening, nucleic acid sequencing, structural control and analysis of RNA/DNA and proteins, medical diagnosis, and magnetic particle susceptibility and size homogenization for other medical applications.

24 Claims, 8 Drawing Sheets

U.S. PATENT DOCUMENTS

2005/0100930 A1     5/2005   Wang et al.
2006/0020371 A1     1/2006   Ham et al.

OTHER PUBLICATIONS

Choi et al., "Development and characterization of a generic microfluidic subsystem toward portable biochemical detection", Micro Total Analysis Systems, 2000, pp. 327-330.*

Choi et al., "An integrated microfluidic biochemical detection system with magnetic bead-based sampling and analysis capabilities", Micro Electro Mechanical Systems, The 14th IEEE International Conference, Jan. 2001, pp. 447-450.*

Graham et al., "Single magnetic microsphere placement and detection on-chip using current line designs with integrated spin valve sensors: Biotechnological applications", Journal of Applied Physics, May 15, 2002, vol. 91, pp. 7786-7788.*

Ferreira et al., "Biodetection Using Magnetically Labeled Biomolecules and Arrays of Spin Valve Sensors," J. of Appl. Physica, May 15, 2003, vol. 93, pp. 7281-7286.

Freitas et al., "Magnetoresistive Biochips," Euorphysics News, 2003, vol. 34, No. 6, pp. 1-8.

Gao et al., "A Study of Magnetic Interactions of Ni80Fe20 Arrays Using Ultrasensitive Microcantilever Torque Magnetometry," J of Appl. Physice, Jun. 1, 2004, vol. 95, pp. 7010-7012.

Graham et al., "Magnetroresistive-Based Biosensors and Biochips," Trends in Biotechnology, Sep. 2004, vol. 22, pp. 455-462.

Grutter et al., "Batch Fabricated Sensors for Magnetic Force Microscopy," Appl. Physics Letters, Oct. 22, 1990, vol. 57, pp. 1820-1822.

Joshi et al., "Biochemical Stability of Components for Use in a DNA Detection System," IEEE Transactions on Magnets, Jul. 4, 2004, vol. 40, pp. 3012-3014.

Li et al., "Detection of a Singel Micro-Sized Magnetic Bead and Magnetic Nanoparticle Using Spin Valve Sensors for Biological Applications," J of Appl Physice, May 15, 2003, vol. 93, pp. 7557-7559.

Li et al., "Spin Valve Sensors for Ultrasensitive Detection of Superparamagnetic Nanoparticles for Biological Applications," Sensors and Actuators A, 2006, vol. 126, pp. 98-106.

Mirowski et al., "Lateral manipulation of Magnetic Particles in a Microfluidic Platform of Arrayed Magnetic Elements: the Road to High Throughput Sorting and Probing of Biological Molecules," Annual APS March Meeting 2004, Mar. 22-26, 2004 Montreal, Quebec, Canada.

Mirowski et al., "Integrated Microfluidic Isolation Platform for Magnetic Particle Manipulation in Biological Systems," App. Physics Letters, Mar. 8, 2004, vol. 84, pp. 1786-1788.

Mirowski et al., "Manipulation and Sorting of Magnetic Particles by a Magnetic Force Microscope on a Microfluidic Magnetic Trap Platform," Appl. Physics Letters, 2005, vol. 86, pp. 243901-1-243901-3.

Moreland, "Nanoprobe Imaging," Electronics and Electrical Engineering Laboratory, Magnetic Technology Divisoin Programs, Activities, and Accomplishments, Jan. 2003, pp. 14-20.

Moreland, "Micromechanical Instruments for Ferromagnetic Measurements," J of Phys D: Applied Physics, 2003, vol. 36, pp. R39-R51.

Ramachadran et al., "Direct and Controlled Manipulation of Nanometer-Sized Particles Using Non-Contact Atomic Force Microscopy," Nanotechnology 1998, vol. 9, pp. 237-245.

* cited by examiner

MICROFLUIDIC PLATFORM OF ARRAYED SWITCHABLE SPIN-VALVE ELEMENTS FOR HIGH-THROUGHPUT SORTING AND MANIPULATION OF MAGNETIC PARTICLES AND BIOMOLECULES

RELATED APPLICATION

This application is a divisional application of U.S. patent application Ser. No. 11/061,461, filed Feb. 18, 2005 to which priority is claimed under 35 U.S.C. §120.

TECHNICAL FIELD

The present invention relates to systems and processes for trapping, manipulating and releasing magnetic particles and biological or chemical species that are coupled to or tagged with magnetic particles. More particularly, the present invention is directed to microfluidic platforms that include one or more spin-valve elements in an array that can be operated to trap, manipulate and release various biological or chemical species.

BACKGROUND ART

The ability to manipulate chemical and biological species on a microscale is an important tool that enables a variety of applications in the fields of biotechnology, microanalysis, microsynthesis, and similar technologies. Depending on the application, useful manipulations may involve separating, transposting, positioning and/or storing various chemical and biological species.

Conventional microfluidic systems that have been used to manipulate chemical and/or biological species have involved controlling fluid flow on a microscale. Chemical or biological species that are suspended in the fluid may thus be manipulated. In some microfluidic systems, pumps and/or valves are used to control fluid flow through a series of physical microchannels formed within a substrate. Such systems are not easily fabricated, have complex structures, and are not easily reconfigured for different operations or dynamica.

High gradient magnetic separation is a long established procedure for selectively retaining magnetic materials in a chamber or column disposed in a magnetic field. This technique has also been applied to non-magnetic targets such as biological materials that are labeled or tagged with magnetic particles. In high gradient magnetic separation a target analyte within a complex sample is labeled with a magnetic material through association with a specific binding ligand that is conjugated to a coating on the particle. The target analyte coupled to the magnetic label is suspended in a fluid which is placed in a chamber or passed through a column and a magnetic gradient is applied to the chamber or column. In the presence of the magnetic gradient the magnetically labeled target analyte is retained while materials that do not have magnetic labels pass through the chamber or column. The retained target analyte can then be eluted by changing the strength of, or eliminating, the magnetic field.

High gradient magnetic separation chambers or columns typically contain a matrix of magnetically susceptible material such as steel wool or wire matrix. When a magnetic field is applied across the chamber, a high magnetic field gradient will be locally induced within the chamber close to the surface of the matrix, permitting retention of the fairly weakly magnetized analytes.

Typical magnetic particle sorting applications include separation of biological analytes such as cells, proteins, and DNA. The premise of the sorting is to attach a chemically functionalized magnetic particle to a desired biological specimen and then apply a magnetic field gradient to pull the magnetic particles away from the solution, thereby leaving the unwanted molecules behind. In this case, sorting is done as an ensemble and single particle location specificity as an end result is not achievable. Single particle sorting techniques have recently been demonstrated based on magnetic wires or domain wall tips. The limitations of these techniques are power consumption and the particles cannot be sorted into an array for long periods of time without causing local heating and hence, possible damage to the samples.

In addition to techniques that are used to sort biological and chemical particles, there are techniques that allow for the manipulation of such particles. Such techniques allow for altering the physical or chemical reaction pathways that occur in biological organisms at the most fundamental level.

The application of lateral and torsional forces to biomolecules by tethered magnetic particles has been an essential method for revealing information about molecular motors, protein-DNA interactions, and the forces associated with folding and unfolding dynamics of DNA. In these experiments, one end of the biological molecule is immobilized onto a microscope slide while the other is attached to a magnetic particle that follows the field gradients generated by macroscopic rare earth magnets. These techniques are generally limited by the fact that the sample must be immobilized and the information obtained is via constant force on the magnetic particle.

There are many different approaches to single molecule measurement and manipulation: atomic force microscopy, micropipettes, electrophoretic translocation, and optical and magnetic tweezers. The geometry that is characteristic to each technique limits the throughput capabilities of the technique as well as the type of biological or chemical system which can be studied. Among the many techniques, tweezers technologies have proven amenable to studying a variety of systems ranging from DNA elasticity to molecular motor dynamics while preserving throughput capabilities, thereby making it one of the more powerful single molecule techniques currently available.

Single molecule tweezers technologies have been developed and widely used to study information about the behavior of individual biological molecules that is otherwise obscured by the statistics of ensemble measurements. A few examples include: 1) how the recognition of protein binding sites and enzymatic work on DNA is affected by the physical conformation (i.e. supercoiling) of DNA; 2) how the function that DNA plays in living cells is directly related to the torsional stress it undergoes in them (altering this conformation often proves lethal to the cells functions); 3) the ability to apply torsional force to molecular motors can lead to information about the energy production of the motor and its enzymatic role in a cell; and 4) rotation of DNA during transcription by RNA polymerase opens the possibility of resolving individual transcription steps.

The more versatile tweezers technologies include optical and magnetic tweezers. Optical tweezers involve tethering biological molecules to dielectric spheres (i.e. handles) and then capturing the spheres at the focal point of an electric field gradient. These tweezers can selectively manipulate a single molecule and manipulate each end of a molecule independently. Despite the utility associated with optical tweezers, manipulation is limited to lateral displacement with a low throughput, and force measurements are limited by the laser power, the difference between the refractive indices of the object and its surrounding medium, and the object dimensions.

Alternatively, magnetic tweezers trap magnetic micro-particles in tailored magnetic field gradients. Due to the magnetic anisotropy inherent in the particles, rotation of the magnetic poles generating the magnetic field gradients that capture the particles imparts torque to the micro-particles and, consequently, to any biological molecule attached to the micro-particles. This torsional motion can be used to stretch, twist, or uncoil biological molecules. The size of the particle used in this set-up can be smaller than that used in optical tweezers and are typically compatible with invivo restrictions. A disadvantage with this type of tweezers is that one end of the biological molecules must be attached to a fixed point, typically a microscope slide.

Currently, most single molecule manipulation techniques are limited to studying one molecule at a time, which limits the throughput to typically one molecule per apparatus per day. In the case of magnetic tweezers, permanent immobilization of the molecule, which hinders the molecule from being moved for further analysis or exploitation, is necessary for performing experiments.

DISCLOSURE OF THE INVENTION

According to various features, characteristics and embodiments of the present invention which will become apparent as the description thereof proceeds, the present invention provides a microchip based platform that allows for high-throughput analysis of individual biological, biochemical or chemical particles, including polymers, molecules and groups of such particles without impairing the mobility of the sample and while ensuring adequate spacing between particles or molecules so that a large number of individual and parallel experiments can be performed on a rapid time scale.

The present invention further provides a high-throughput and low power consumption platform for sorting and probing biopolymers and other biological molecules, chemical compounds, etc one or more molecules at a time.

The present invention also provides methods and apparatuses that allow temporary and selective immobilize of individual samples in a discrete matrix.

The present invention further provides for methods and apparatuses for applying torsional forces to individual biological, biochemical or chemical particles, polymers and molecules.

The present invention also provides for methods and apparatuses for applying rotational forces to individual biological, biochemical or chemical particles, polymers and molecules.

According to one specific embodiment, the present invention provides a microfluidic platform for selectively capturing and releasing magnetic particles which includes:

a substrate supporting a membrane over at least one opening in the substrate; and a plurality of spin-valve elements provided on a supported portion of the membrane, the plurality of spin-valve elements each comprise a discrete layer of a material that, when subjected to an applied magnetic field produces a local magnetic field that is capable of attracting and restraining magnetic particles near the spin-valve elements.

According to another embodiment, the present invention provides a spin-valve platform that includes:

a membrane having opposite side surfaces; and a plurality of spin-valve elements provided one of the opposite side surfaces of the membrane, the plurality of spin-valve elements each comprising a discrete layer of a material that, when subjected to an applied magnetic field produces a local magnetic field that is capable of attracting and restraining magnetic particles near the spin-valve elements.

According to yet another embodiment, the present invention provides a method of manipulating magnetic particles which involves:

providing a plurality of magnetic particles;

dispersing the magnetic particles in a fluid;

providing an array of spin-valve elements which comprise discrete substantially coplanar layers of a material that, when subjected to an applied magnetic field produces a local magnetic field that is capable of attracting and restraining magnetic particles near the spin-valve elements;

applying an applied magnetic field to the array of spin-valve elements; and bringing the fluid having the magnetic particles dispersed therein near the array of spin-vale elements so that at least one or more of the magnetic particles are held by the local magnetic fields of one or more of the spin-valve elements.

BRIEF DESCRIPTION OF DRAWINGS

The present invention will be described with reference to the attached drawings which are given as non-limiting examples only, in which.

BEST MODE FOR CARRYING OUT THE INVENTION

Figure 1:
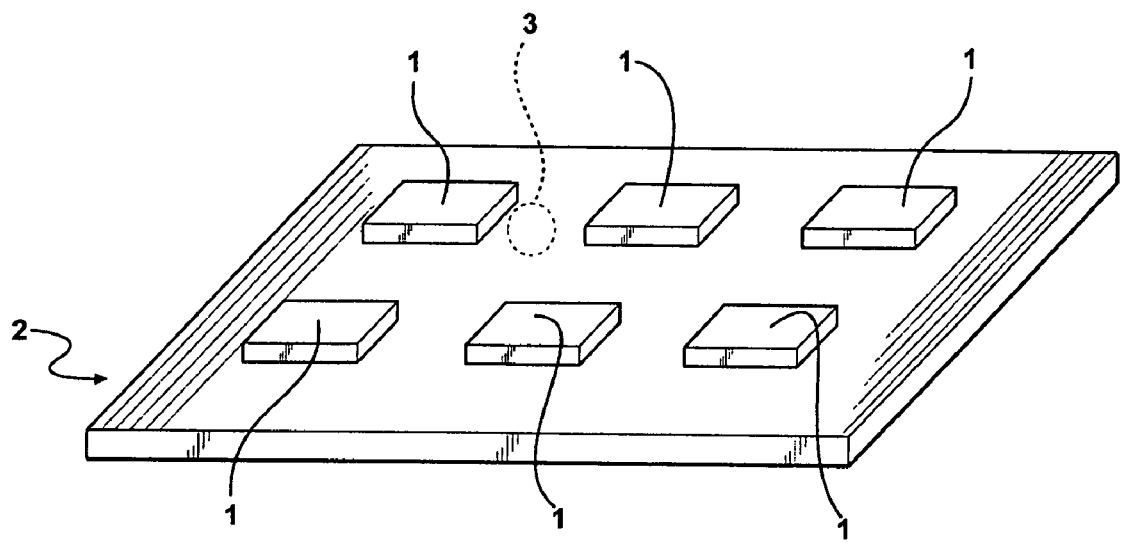
FIG. 1 is a perspective view of a portion of a micromachined magnetic trap platform according to one embodiment of the present invention.

The present invention provides a microfluidic platform that incorporates a platform consisting of a super array of spin-valve arrays each including arrays of individual spin-valve elements that can be used to selectively trap, manipulate and release magnetic or magnetically tagged or labeled particles with high throughput and specificity. Each array of spin-valve elements as well as each spin-valve element can exist in a ferromagnetic "ON" state in which the individual spin-valve elements act like micro bar magnets with local magnetic fields. The magnetic field gradients provide the trapping field to confine the magnetic particles. The spin-valve platforms and spin-valves can be turned to the antiferromagnetic "OFF" state where the spin-valves no longer produce a local magnetic field. In the absence of the local magnetic field, the magnetic particles are released from the spin-valve elements. The platform consists of a membrane that can separate the spin-valve arrays and spin-valve elements from the magnetic particle fluid, or it is possible to have the magnetic particle fluid on the same side of the spin-valve platforms and spin-valve elements. The "ON/OFF" magnetic characteristic of the spin-valve platforms and spin-valve elements make it possible to apply an applied global magnetic field to rotate the magnetic particles or apply torsion or tension to the magnetic particles while they are confined by the spin-valve elements. This invention may be used in a variety of applications including drug screening, nucleic acid sequencing, structural control and analysis of RNA/DNA, medical diagnosis, and magnetic particle susceptibility and size homogenization for medical applications.

The present invention provides a means by which to trap, measure, manipulate, sort and release magnetic particles with reproducible location specificity and high throughput.

The present invention further provides methods of manipulating magnetic or magnetically tagged or labeled particles by changing the alignment or strength of applied magnetic files or by the use of magnetic tweezers.

Since magnetic particles can be attached to biological molecules, these characteristics can be applied to biological systems including biopolymers or to chemical species where individual cells or molecules can be sorted, measured, rotationally and laterally manipulated, and released. It is to be understood that the term "magnetic particles" is used herein to encompass magnetically tagged and magnetically labeled biological and chemical species in reference to how the spin-valve arrays and spin-valve elements of the present invention function and are used.

The present invention consists of a microfluidic platform that includes a transparent membrane that acts as a barrier between the spin valve arrays and the fluid. The membrane can also be opaque. The membrane can be partially supported or completely supported by the substrate. The spin-valve elements can be formed on the membrane, opposite the fluid or the fluid can be on the same side as the spin-valve arrays. The array of spin-valve elements can be magnetized all at once by applying a macroscopic applied magnetic field for a duration of time or individually by applying a current pulse through a spin valve element or by applying momentary current to a set of wires in close proximity to each individual spin-valve element. The spin-valve elements then remain in a ferromagnetic "ON" state in the absence of an applied magnetic field. In this state, magnetic particles or particles that are magnetically tagged or labeled are trapped in the local magnetic field gradient of each spin-valve element indefinitely. In the "ON" state a second magnetic field of sufficient strength to rotate the particles but insufficient to change the ferromagnetic character of the spin-valve elements, can be applied to provide torsional/rotational manipulation to objects (e.g. biological specimens, chemical compounds, etc.) that can be attached to the magnetic particles. Since the spin-valve elements are arrayed as are the spin-valve arrays, the location of trapped particles can be specified by a matrix position with respect to all other spin-valve elements and spin-valve arrays in a platform.

Figure 2:
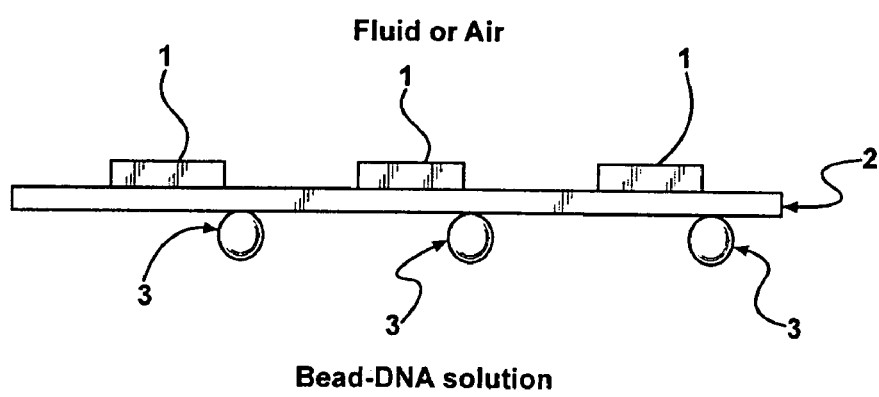
FIG. 2 is a cross sectional view of the micromachined magnetic trap platform of FIG. 1.

FIG. 1 is a perspective view of a portion of micromachined magnetic trap platform (also referred to herein as a microfluidic platform) according to one embodiment of the present invention. FIG. 2 is a cross sectional view of the portion of the micromachined magnetic trap platform of FIG. 1.

The basic micromachined magnetic trap platform includes an array of spin-valve elements each of which includes an array of spin-valve traps 1. As will be understood from the description of FIG. 3E below, the micromachined magnetic trap platform can include a silicon wafer substrate that supports an array of suspended membrane areas which are referred to herein as spin-valve elements, each of which includes an array of spin-valve traps 1 as depicted in FIGS. 1 and 3. The spin-valve traps 1 are supported on a membrane 2 or other suitable substrate that can provide a fluid barrier as discussed below. The spin-valve traps 1 comprise a layer of a material that can produce a local magnetic field when an external magnetic field is applied thereto. An example of such a material is as PERMALLOY™ ($Ni_{80}Fe_{20}$). The membrane 2 can be a fluid impermeable membrane that acts as a barrier between the spin-valve traps 1 and a fluid containing magnetic particles. The membrane 2 can be transparent or opaque and made from a material that provides a fluid barrier. According to one embodiment of the present invention a silicon nitride membrane was determined to be suitable for use with biological samples. Transparent membranes were determined to be particularly useful because they allow for the simultaneous incorporation and application of optical techniques. For example, a transparent membrane would allow for the micromachined magnetic trap platform that supports the spin-valve elements and spin-valve traps 1 to be placed on an inverted optical microscope for observation of translocation events. The optical microscope can be equipped with a charge-coupled device (CCD) camera and imaging software. The images obtained by the CCD camera could provide information on the location of the magnetic particles with respect to the spin-valve traps. By interfacing the CCD image with the MFM software, a program can be implemented to sort particles, based on size, color, chemical functionality, and magnetic susceptibility, into their respective positions in an array.

A liquid sample solution can be injected beneath the membrane 2, opposite the magnetic traps 1, or on the same side of the membrane 2 as the magnetic traps 1.

When the micromachined magnetic trap platform of FIG. 1 is placed in an applied magnetic field, the trap arrays are induced to create local magnetic fields that are localized about each individual trap 1. As depicted in FIG. 2, magnetic particles 3 or magnetically tagged or labeled particles become attracted and trapped in the individual magnetic fields that are localized about the magnetic traps 1.

FIGS. 3A-3E depict on manner of fabricating the micromachined magnetic trap platform of FIG. 1.

Figure 3A:
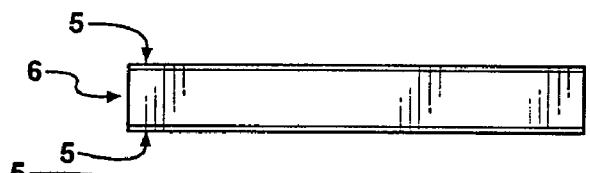
FIGS. 3A-3E depict one manner of fabricating the micromachined magnetic trap platform of FIG. 1.
Figure 3B:
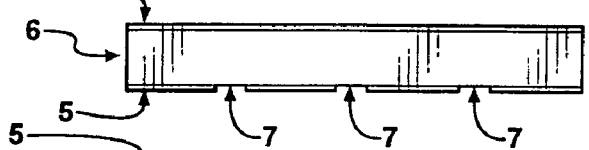
Figure 3C:
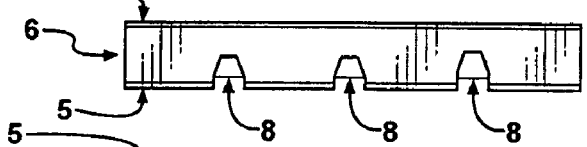
Figure 3D:
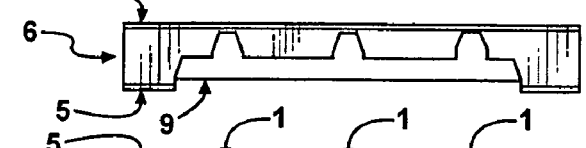
Figure 3E:
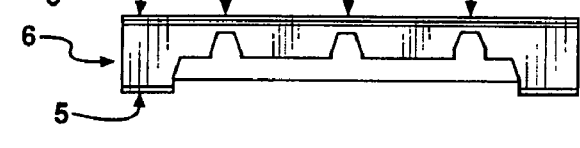

According to one embodiment of the present invention the micromachined magnetic trap platform (also referred to as a microfluidic platform) can be fabricated as depicted in FIGS. 3A-3E by depositing a 0.2-1 μm low stress silicon nitride 5 on opposite sides of a polished 350 μm Si (100) wafer 6 as depicted in FIG. 3A. Next, an array of 0.014 $mm^2$ squares 7 are etched in the nitride film 5 on the back side of the wafer 6 as depicted in FIG. 3B followed by anisotropically etching wells 8 in the underlying silicon to the nitride film 5 on the opposite side of the wafer 6 as depicted in FIGS. 3C using, for example, aqueous potassium hydroxide. After wells 8 are formed, fluid channels 9 can be formed in the silicon wafer 6 as depicted in FIG. 3E. Next, the magnetic traps 1 were formed using a photoresist and sputter depositing a tantalum adhesive layer of 5 μm and a PERMALLOY™ layer of 30 μm as depicted in FIG. 3F. The arrays of traps 1 etched across each portion of the nitride membrane that extends across the bottoms of each of the wells 8 is referred to herein as the spin-valve elements. The individual traps 1 are referred herein to as traps or spin-valve traps. From FIGS. 3A-3E it can be understood that a single chip or micromachined magnetic trap platform can include a plurality of spin-valve elements (arranged in an array) each or which includes a plurality of spin-valve traps 1 that are also arranged in an array.

According to the present invention micromachined magnetic trap platforms can have a plurality of magnetic trap arrays each of which can have 50 to 200 traps with each trap being 1.2 μm×3.6 μm, it being understood that these dimensions and number or traps are non-limiting examples only and that the dimensions and number or traps can easily be varied as desired.

The single layered traps of FIGS. 1-3 (not counting the tantalum adhesive layer, can be activated (stitched "ON" or "OFF") by application of an applied magnetic field. According to further embodiments of the present invention multilayered spin-valve traps are provided which can be switched "ON" and "OFF" in groups or individually by application of an auxiliary magnetic field that can be applied selectively and as a short pulse as discussed below.

Figure 4:
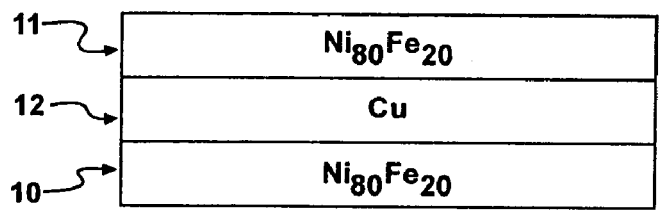
FIG. 4 is a schematic side view of a spin-valve trap according to one embodiment of the present invention.

FIG. 4 is a schematic side view of a spin-valve trap according to one embodiment of the present invention. The spin-valve trap depicted in FIG. 4 includes two layers of magnetic permeable or ferric material exemplified as PERMALLOY™ 10, 11 which are separated by an intermediate layer of copper 12. Note shown in FIG. 4 is a lower layer of tantalum which would normally be provided as an adhesive layer to secure the multilayered spin-valve trap to a membrane.

Figure 5:
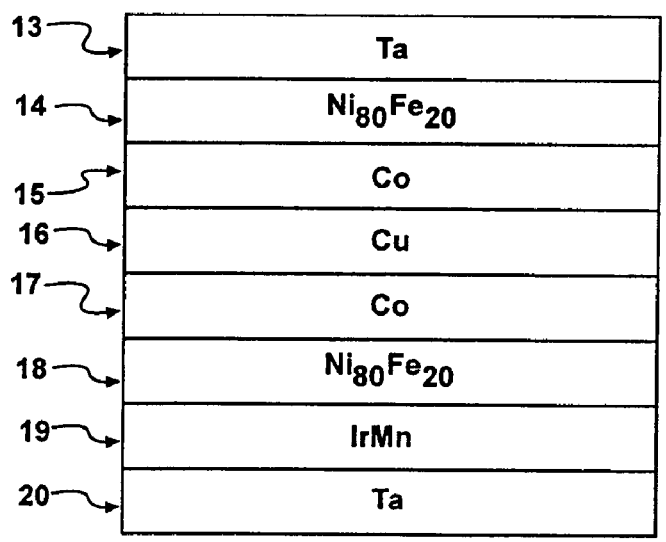
FIG. 5 is a schematic side view of a spin-valve trap according to another embodiment of the present invention.

FIG. 5 is a schematic side view of a spin-valve trap according to another embodiment of the present invention. The spin-valve trap depicted in FIG. 5 includes a layer of tantalum 13, a layer of PERMALLOY™ ($Ni_{80}Fe_{20}$) 14, a layer of cobalt 15, a layer of copper 16, a layer of cobalt 17, a layer of PERMALLOY™ ($Ni_{80}Fe_{20}$) 18, a layer of IrMn 19 and a later of tantalum 20 as shown. According to one embodiment the layer 13 of tantalum was 5 nm, the layer 14 of PERMALLOY™ ($Ni_{80}Fe_{20}$) was 15 nm, the layer 15 of cobalt 5 nm, the layer 16 of copper was 10 nm, the layer 17 of cobalt was 5 nm, the layer 18 of PERMALLOY™ ($Ni_{80}Fe_{20}$) was 15 nm, the layer 19 of IrMn was 5 nm and the layer 20 of tantalum was 5 nm. The lower layer of tantalum 20 functions as an adhesive between the spin-valve trap and the membrane to which is attached and the top layer of tantalum 13 acts as a barrier to oxidation. The cobalt layers 15 and 17 act as diffusion barriers between the PERMALLOY™ ($Ni_{80}Fe_{20}$) layers 14 and 18 and the Cu spacer layer 16. According to one embodiment, a spin-valve trap as illustrated in FIG. 5 was fabricated having a width of 1 micrometer in width and a length of 4 micrometers. It is to be understood that the dimensions of the elements discussed herein including the spin-valve elements and spin-valve traps and the thickness of the various layers of the spin-valve traps and membrane are not limited to the specific examples given and could be varied as desired.

Figure 6:
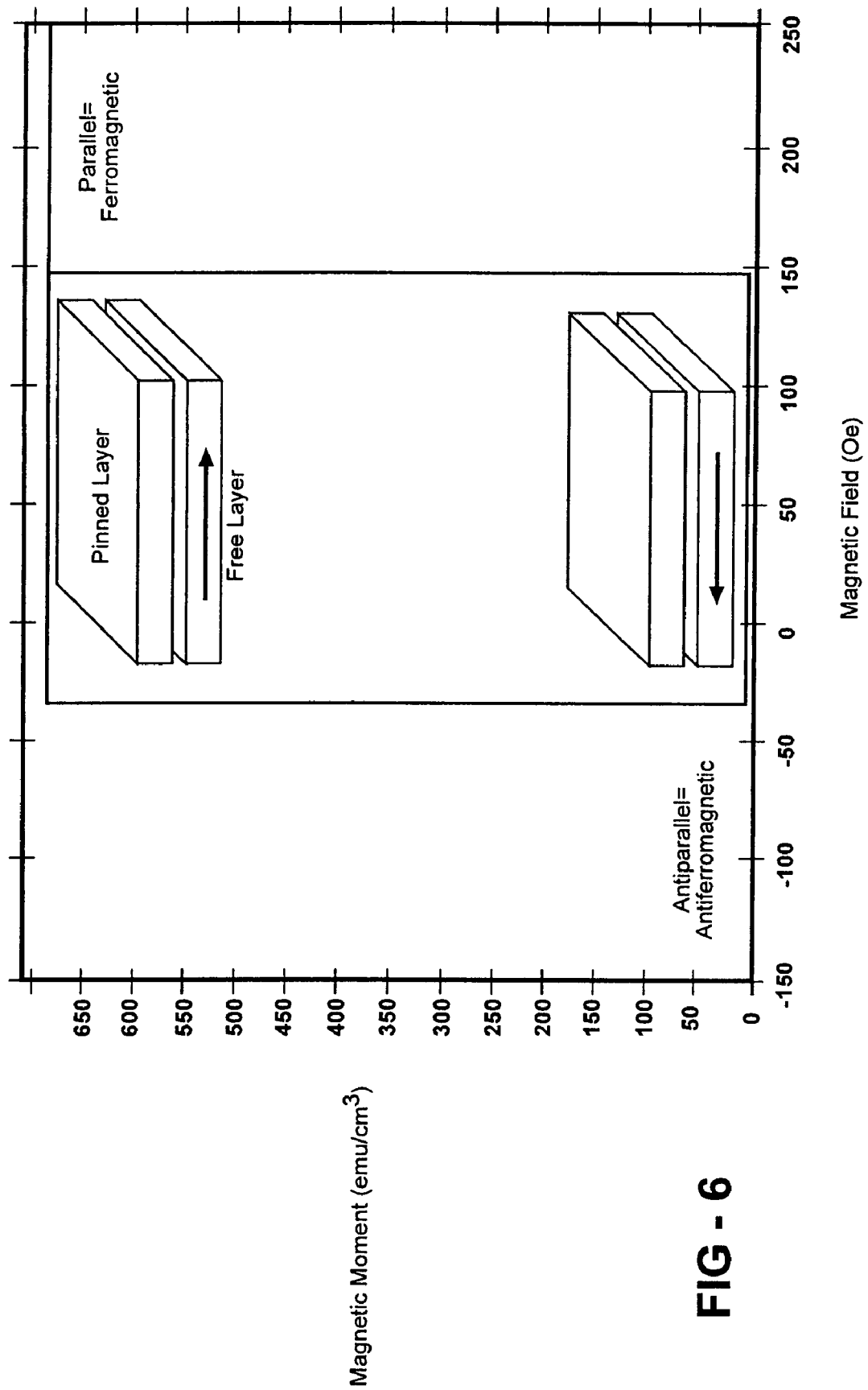
FIG. 6 is an M-H curve of a spin-valve element according to one embodiment of the present invention.

FIG. 6 is an M-H curve of a spin-valve element that depicts the bistable state at H=0 Oe. As shown in FIG. 6, the spin-valve elements exhibit a bistable magnetic structure that encompasses a ferromagnetic "ON" and antiferromagnetic "OFF" state in the absence of an applied magnetic or current-induced magnetic field. Since the spin-valve arrays and spin-valve elements are arrayed, the location of the traped particle can be specified by a matrix position with respect to all other spin-valve arrays and spin-valve elements in the arrays. The magnetization of the spin-valve elements can be macroscopically turned "ON" and "OFF" by applying an applied magnetic field of the appropriate magnitude and polarity or individually turned "ON" and "OFF" by applying the appropriate current-induced magnetic fields to each individual spin-valve array or each individual spin-valve element.

Figure 7:
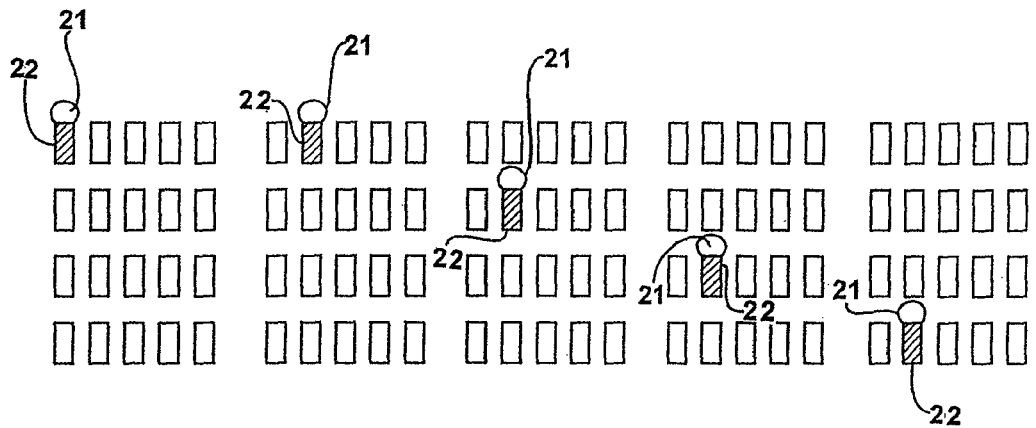
FIG. 7 depicts how magnetic particles are can be sorted and positioned in a stationary array by one of the spin-valve elements of the present invention.

In the "OFF" state, the spins in the free layer of each spin-valve element are aligned antiparallel to the spins in the pinned layer. The fields from each layer cancel one another effectively leaving the trap non-magnetic in nature. In this case, particles would not be attracted to the trap and would be free to seek out the closest region with a high magnetic field gradient. In the "ON" state, the free layer in the trap is aligned with the pinned layer, thereby producing a magnetic field gradient that is strongest at the ends of the trap. In this state, the particles are trapped in the local magnetic field gradient of each spin-valve element. When using current induced magnetic fields, each individual spin-valve arrays or individual spin-valve elements can be turned "ON" and "OFF". The proper sequence of "ON/OFF" events produces sorting of magnetic particles by the stationary array of spin-valve elements in any portion of its respective spin-valve array as illustrated in FIG. 7 where the magnetic particles 21 are depicted as being attached to spin-valve elements 22 that are in their "ON" state. In addition, magnetic particles can be moved between adjacent spin valve elements with an appropriate pulse sequence. Finally, a movable tip with a spin-valve element on the end can also be used to sort the particles as discussed in more detail below.

Since there is a minimum magnetic field necessary to flip between states, a second magnetic field can be applied to systems of the present invention that include multilayered spin-valve elements. For example, in the "ON" state, a second magnetic field of sufficient strength to rotate the particle, but of insufficient strength to change the ferromagnetic character of the spin-valve arrays or relevant traps, can be applied to provide torsional/rotational manipulation to samples (e.g. biological specimens, chemical compounds, etc.) that can be attached to the trapped magnetic particles.

Figure 8A:
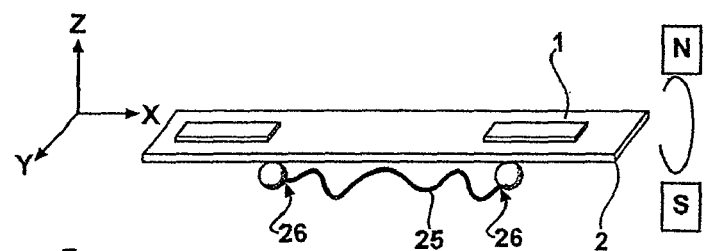
FIGS. 8A-8C depict how a biopolymer (DNA) that is held by opposite ends by separated spin-valve elements can be rotated about various coordinate axes.
Figure 8B:
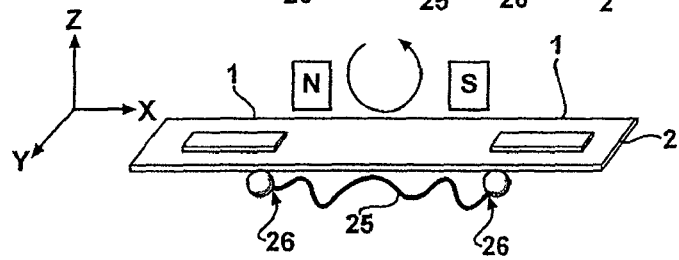
Figure 8C:
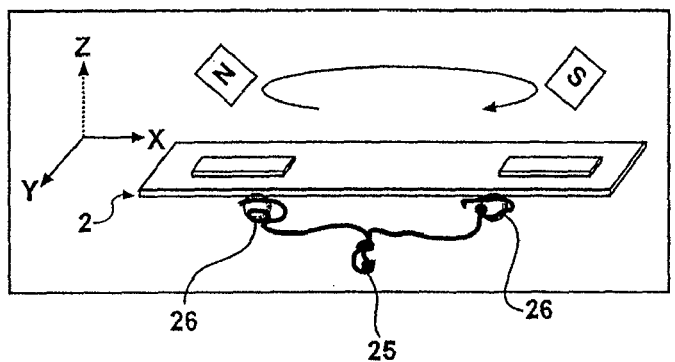
Figures 9A, 9B, 9C:
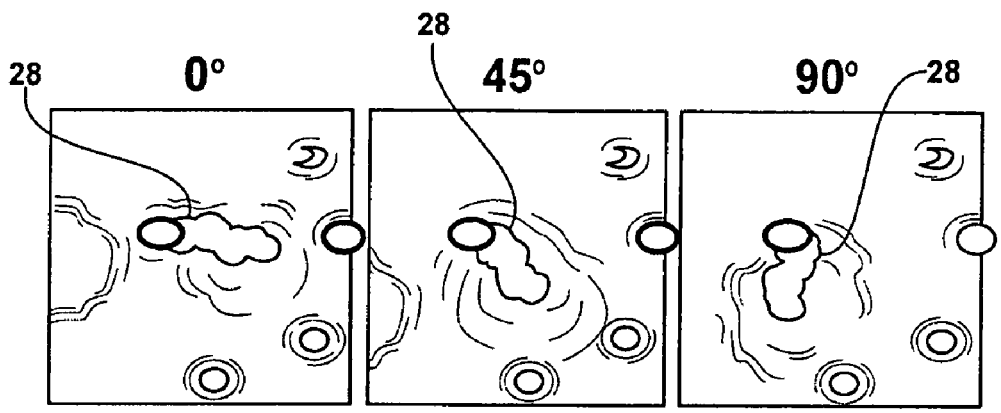
FIGS. 9A-9I depict a sequence of a magnetic particle confined by a field gradient produced by a spin-valve element during rotation of an applied auxiliary magnet field.
Figures 9D, 9E, 9F:
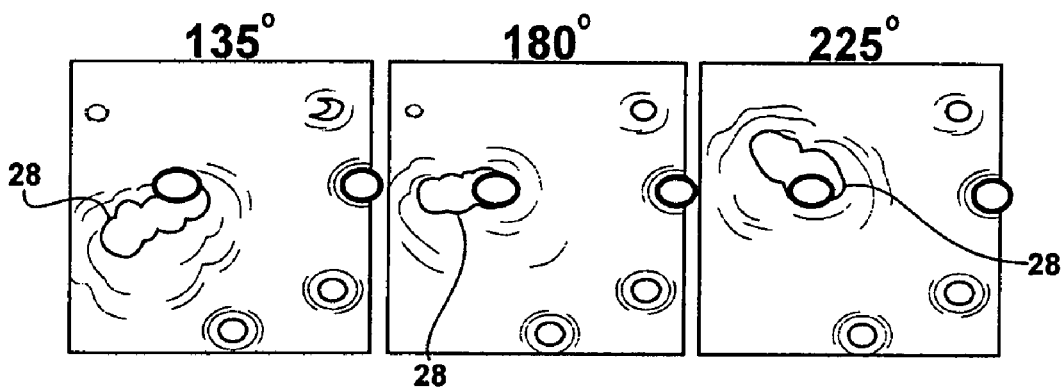
Figures 9G, 9H, 9I:
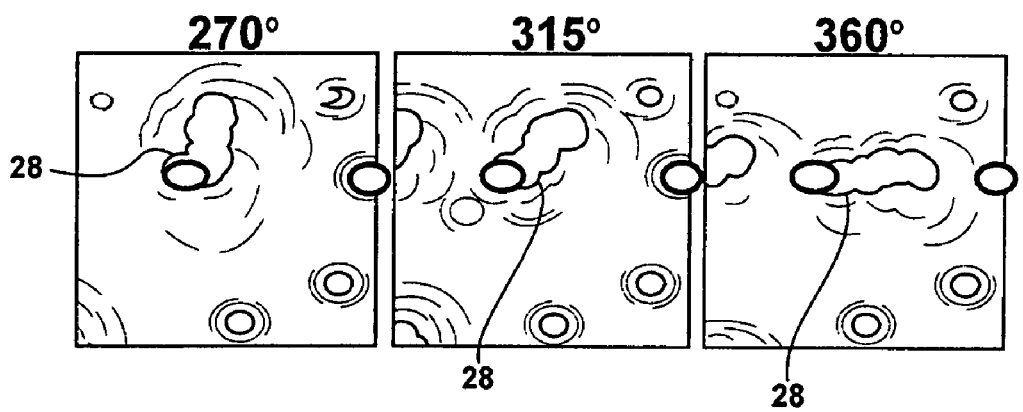

FIGS. 8A-8C depict various geometries for the application of a rotational magnetic field to a biopolymer (DNA) 25 that is held by opposite ends 26 by separated spin-valve traps 1. The rotation of the magnetic field can be about the X, Y or Z axes. Since the direction of rotation (i.e., clockwise or counterclockwise) is the same for all particles, rotation about the Y and X axes (FIGS. 8B and 8A) will not allow for the application of torque to biological molecules 25. For rotation about the X-axis, the entire molecule 25 will rotate about a fixed point as indicated in FIG. 8A. For rotation about the Y-axis, it is possible for the molecule 25 to flip to alleviate the any applied torsional force as indicated in FIG. 8B. For rotation about the Z-axis, torsional force can be applied to the molecule 25 as depicted in FIG. 8C. For this geometry, it is noted that the attachment points of the molecule 25 to the magnetic particle point must both point away from the membrane surface. This can be accomplished by providing steric hinderance in the form of small grooves in the membrane.

According to experiments conducted during the course of the present invention, a rotational field of approximately 12 Oe with a 0.003 T/cm magnetic field gradient was determined to be sufficient to rotate particles about spin-valve elements in an array of a spin-valve element. The small magnitude of the rotational field had a negligible effect on the trap magnetization state since the minimum field required to flip the state of the spin-valve was 15 Oe. FIGS. 9A-9I depict a sequence of a magnetic particle confined by the field gradient produced by a spin-valve element during rotation of the magnets about the platform. To visually demonstrate the rotation of the magnetic particles, a strand of particles 28 was used instead of individual particles in FIGS. 9A-9I. The length of the strands was four particles, the first of which is trapped in the field gradient to the right of the spin-valve element. As the magnetic field was rotated, the line of particles followed the field. For angles of 135° to 270°, the length of the strand of magnetic particles appears shorter. This is due to the fact that the trapped particle remains in its initial location and the strand of particles overlap the spin-valve element and are obscured by it.

The experiments which were conducted to provide the results depicted in FIGS. 8 and 9 above demonstrate that bistable spin-valve elements, in the absence of applied magnetic fields, are capable of confining magnetic particles that are separated from the traps by a membrane and that with the application of a rotating magnetic field gradient, it is possible to rotate magnetic particles while they are confined to a specific location. This ability to rotate confined particles can be used to apply torsional forces to arrays of DNA molecules and other biological specimens, chemical compounds, etc. This ability allows for high-throughput and low power consumption measurement and control of biological and chemical processes on a single molecule level.

According to another aspect of the present invention, which will now be discussed, the microfluidic magnetic trap platform is used with an applied magnetic force microscope (MFM) cantilever. The MFM cantilever tip serves as a magnetorobotic arm that provides a translatable local magnetic field gradient to capture and move magnetic particles with nanometer precision. The MFM electronics can be programmed to sort an initially random distribution of particles by moving them within an array of magnetic trapping elements. The system permits a particle sorting rate of approximately 5500 particles/minute. Release of the particles from the MFM tip is made possible by the membrane that separates the arm and magnetic trap elements from the particle solution. This platform has potential applications for magnetic based sorting, manipulation and probing of biological molecules in a constant displacement or a constant force mode.

In initial experiments using a commercially available cobalt coated MFM tip with a radius of 90 nm, a height of 15 µm, and width at the top of the tip of 10 µm it was discovered that the particles were not strongly attracted to the tip field gradients and did not translate with the tip. This was attributed to the fact that the tip slope was sufficiently large to allow for a diminished interaction between the magnetic material on the sidewall of the tip and the particles. To increase the area of interaction between the tip and the particle, the tip was sanded by scanning it rapidly on a hard surface such as vicinal yttria stabilized cubic zirconia. Scanning electron microscopy images show a sanded tip had a 0.8 µm wide sanded plateau. With this geometry, the magnetic material that produces the field gradient to capture the particles consists of a ring having a 60 nm width and a radius of approximately 400 nm.

Figure 11A:
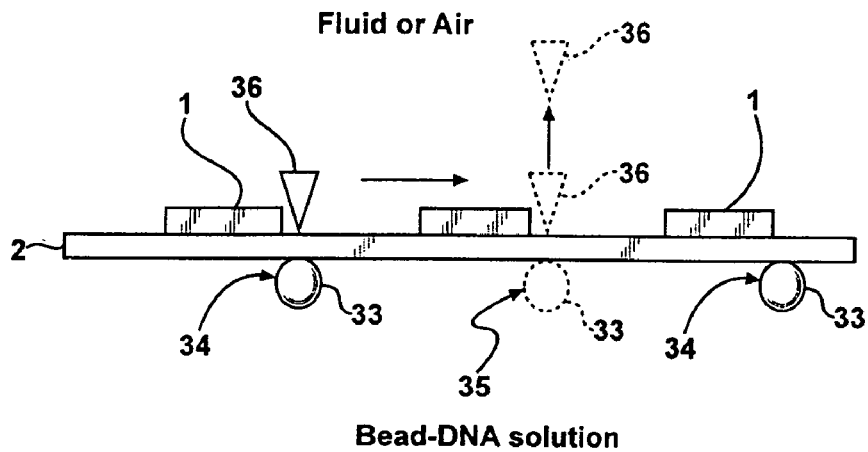
FIG. 11A depicts how a particle can be moved into a desired portion using a magnetic tipped probe.
Figure 11B:
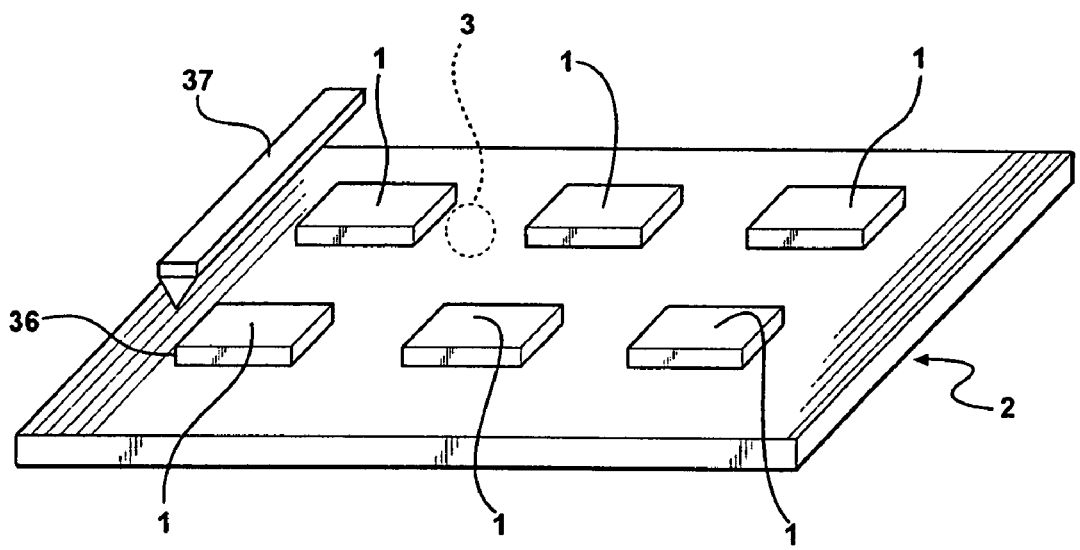
FIG. 11B depicts the magnetic tipped probe and array of spin-valve elements of FIG. 11A in perspective.
Figure 10A:
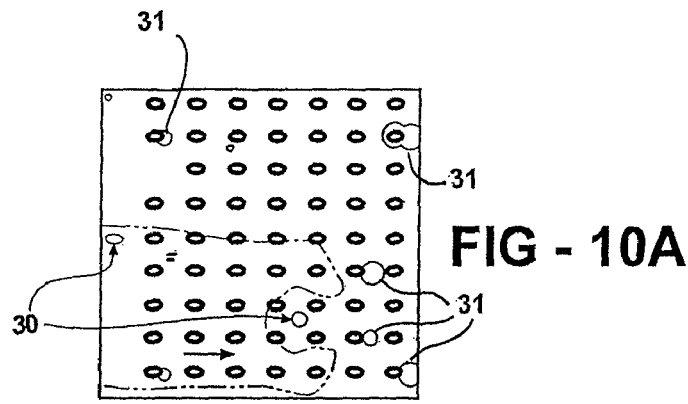
FIG. 10A depicts an initial random distribution of particles before being sorted by an array of spin-valve elements.
Figure 10B:
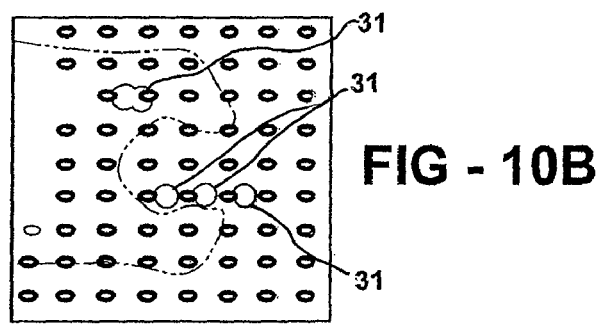
FIG. 10B depicts the particles of FIG. 10A after they have been sorted.

Size sorting experiments were conducted be injecting a solution of 2.8 µm and 5 µm diameter iron and iron oxide embedded polystyrene particles suspended in water into the wells of the microfluidic magnetic trap platform so that the particles were. FIG. 10A depicts an initial random distribution of particles including transit particle 30 and held particles 31, and FIG. 10B depicts the particles after being sorted as all being held. The tip provides the translatable magnetic field gradient while the PERMALLOY™ elements of the spin-valve traps are used to spatially confine the sorted particles. The particles are placed into each sorted position by approaching the surface of the membrane over where the particle to be moved is located. Since the tip field gradients die off as $r^{-3}$, it is necessary to bring the tip as close to the particle to be moved as possible. The minimum distance is limited by the thickness of the membrane which in one experiment was 200 nm; however, it is possible to decrease the thickness of the membrane to 100 nm without damaging the resilience of the membrane. Once the tip contacts the surface, the particle is moved to a predetermined trapping element. To release the particle from the tip field gradient, the tip is retracted from the surface to suitable distance, for example about 9 µm or greater. At this height, the tip then moves to the next particle to be sorted. FIG. 11A depicts how a particle can be moved into a desired portion using a magnetic tipped probe. In FIG. 11A, the particle 33 is moved from an initial position 34 to a new position 35 manipulating the tip 36 of the probe 37 as illustrated and discussed above. FIG. 11B depicts the magnetic tipped probe and microfluidic magnetic trap platform of FIG. 11A in perspective.

Once the particles are placed into desired positions in the array, each particle can be annotated for future manipulation and analysis. Sorting of various sized particles can be accomplished by tailoring of the tip geometry for specific size ranges.

In the case of a tip size of 800 nm, the geometry was optimized for 1 micrometer particles, although larger particles could also be sorted with less efficiency. The maximum velocity at which the particles are translated was measured by rastering the tip in incremental velocities and recording the point at which the magnetic microparticle no longer follows the tip. A maximum translation velocity of 2.2 mm/sec±0.1 mm/sec for a 1 µm particle was measured in this manner. To determine the maximum sorting rate, it was assumed that with an average translation distance of 20 µm, a tip repositioning time of 2 ms and a computer interface time of 1 ms. These approximations were used to calculate a maximum sorting rate of approximately 5500 individual particles can be sorted per minute.

The magnetic homogeneity and smaller size of the 1 micrometer magnetic particles made them a typical choice for magnetic tweezers experiments. To implement a magnetic tweezers platform, a comparison was needed between the forces acting on the particles to conventional tweezers instruments. To determine the force acting on the particles velocity was measured. However, since the particles are near the surface of the membrane, a simple treatment using the Stoke's Law for viscous drag is not appropriate in determining the force acting on the particle. Using the relationship for hydrodynamic drag on a particle positioned at a surface, the force is expressed as $F=1.7005 \times 6\pi\eta r^2 G$, here $\eta$ is the viscosity of the medium, which in this case is water, r the radius of the sphere and G the shear rate of the fluid flow. For this equation to be valid, it must be proven that the test system is under laminar flow conditions. For laminar flow the Reynold's number (Re) for the system must be less than 1, and for the present system Re was calculated as Re=$2.3 \times 10^{-6} \pm 0.1 \times 10^{-6}$ from the velocity measurements made by scanning the tip. Therefore, the shear rate can be calculated under the condition of a uniform velocity gradient by using the velocity of at the center of the sphere, which, in this case, corresponds to the distance from the surface to the center of the sphere. Under these conditions, a shear rate of $4.6 \pm 0.1 \times 10^3$ sec$^{-1}$ was calculated which corresponds to a force of $35.3 \pm 2.0$ pN.

Figure 12:
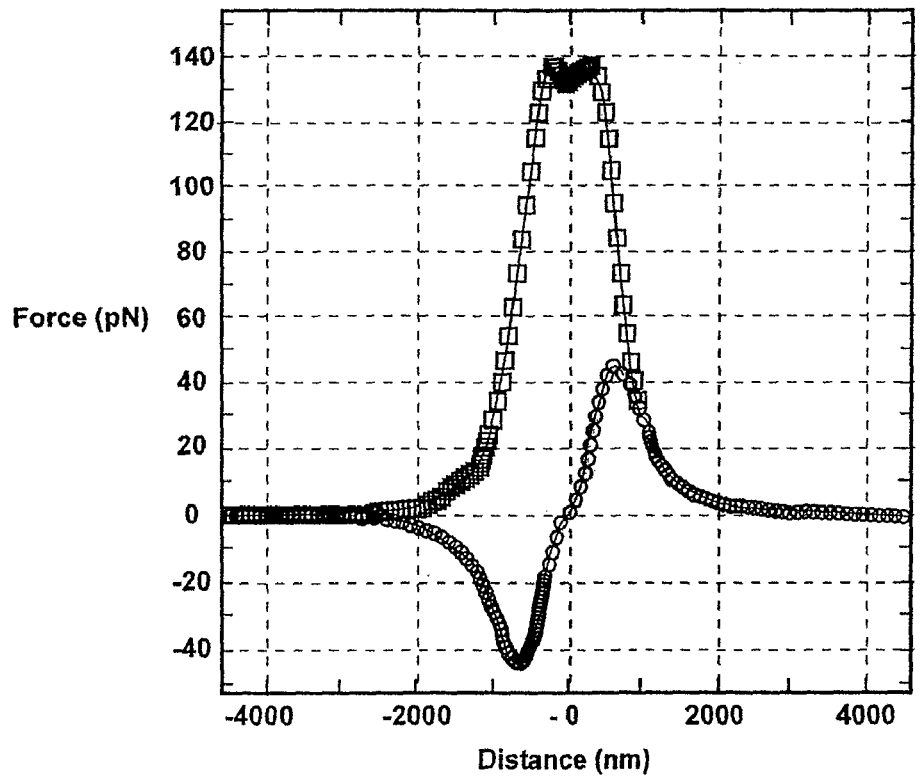
FIG. 12 shows the force versus distance simulations for a conical and truncated tip with an 800 run diameter and a 1 μm diameter magnetic particle.

To confirm the experimental force measurements, micromagnetic simulations were used to calculate the total force acting on the particles. FIG. 12 shows the force versus distance simulations for a conical and truncated tip with an 800 nm diameter and a 1 μm diameter magnetic particle. Simulations confirm that a truncated tip provides a stronger trapping force than a conical tip. For the truncated tip, the maximum lateral force acting on the particles is 45 pN. This value is slightly larger than the experimental value measured during the course of the present invention. Deviations from the experimental values obtained using hydrodynamic drag equation are most likely due to the frictional force resulting from the normal force, $F_z$, pulling the bead into the silicon nitride membrane surface. The force as a function of displacement from the center of the tip indicates that the size of the field gradient is comparable to the size of the particle, and the field outside the particle decreases rapidly. This localization of the magnetic trapping field allows for constant displacement measurements to be made, which is in contrast to typical magnetic tweezers that function as force clamps. While the set-up tested produced forces comparable to optical tweezers, it is possible to tailor the tip-particle geometry and magnetic material used to increase the force acting on the particle to forces typical of current magnetic tweezers apparatus (~$10^2$ pN).

The magnetic material coating the side walls of the cone comprising the tip produces sufficient magnetic field gradients to attract more than one particle at a time. This is an undesirable attribute that can be resolved by implementing the traps to separate the particles. Particles less than 5 μm in diameter that are stuck together may be split up by dragging the particles over the center of a PERMALLOY™ element, where the particle furthest away from the tip will remain with the PERMALLOY™ element, while the other continues to track the field gradient of the tip.

Figure 13:
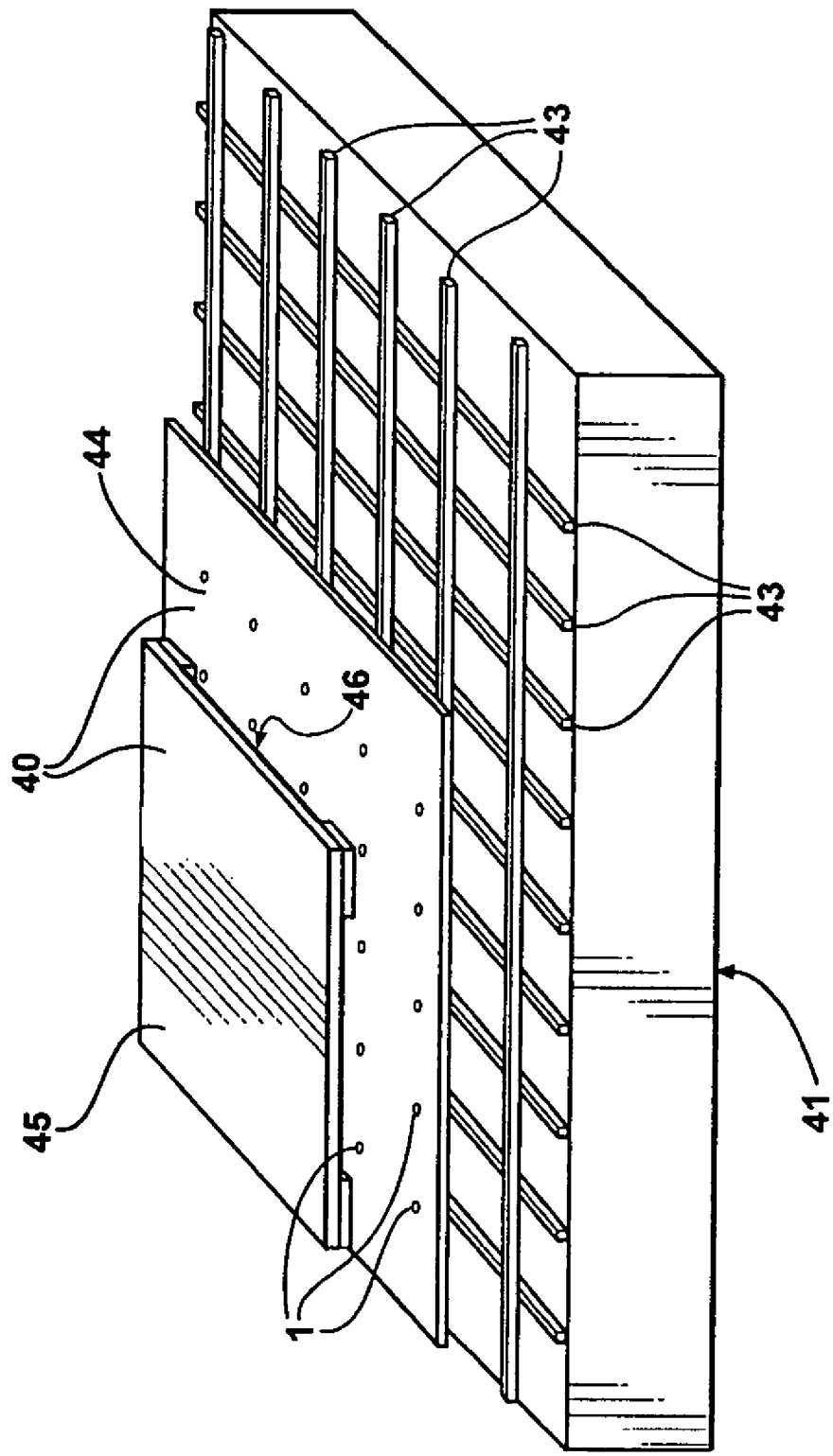
FIG. 13 shows a magnetic random access molecular manipulator according to one embodiment of the present invention.

FIG. 13 depicts a magnetic random access molecular manipulator according to one embodiment of the present invention (Note: will change description of FIG. 13 on page 8 in same manner). In FIG. 13 a micro fluidic chamber 40 that includes an array of magnetic traps 1 according to the present invention is positioned on a magnetic random access memory chip 41 that can be used to individually switch the magnetic traps 1 "ON" and "OFF" by passing current pulses through the magnetic traps or through wires 43 that are configured to address each of the magnetic traps 1. The micro fluidic chamber 40 includes a support 44 for the magnetic traps 1 which can be a fluid permeable support such as a membrane that provides a fluid barrier between the micro fluidic chamber 40 and the underlying electronics package. The micro fluidic chamber 40 can also include a suitable structure 45 that forms a flow area 46 to contain or direct the transfer of a fluid within the micro fluidic chamber 40. Such a structure 45 can be a silicon substrate, membrane or any suitable structure. With reference to FIG. 13 is noted that the present invention allows for the controlled movement of magnetic particles without a fluid flow channel. For example, an open surface provided with the array of magnetic traps 1 and the magnetic random access memory chip 41 of FIG. 13 (or any suitable control of the individual traps) would allow one to selectively turn "OFF" a magnet trap holding a particle and turn "ON" adjacent magnetic traps in sequence to move the particle around as desired. This eliminates the need for the type of fluid flow that is the basis of micro flow channel technology.

Although the present invention has been described with reference to particular means, materials and embodiments, from the foregoing description, one skilled in the art can easily ascertain the essential characteristics of the present invention and various changes and modifications can be made to adapt the various uses and characteristics without departing from the spirit and scope of the present invention as described above and in the attached claims.

What is claimed is:

1. A method of manipulating magnetic particles, which method comprises:
   providing a fluid having a plurality of magnetic particles dispersed therein;
   providing an array of spin valve magnetic traps, each of which comprises discrete substantially coplanar layers of material that, when temporarily subjected to a magnetic field of sufficient strength to change the magnetization state of the spin valve trap to an on state, produces a local magnetic field that is capable of attracting and indefinitely retaining magnetic particles proximate the spin valve magnetic traps;
   bringing the fluid having the magnetic particles dispersed therein proximate the array of spin valve magnetic traps; and
   temporarily subjecting each spin valve magnetic trap to the magnetic field so as to selectively switch between the on state, in which the local magnetic fields are produced and the magnetic particles are magnetically attracted and retained proximate the spin valve magnetic traps, and an off state, in which no local magnetic fields are produced and the magnetic particles are not attracted or retained proximate the spin valve magnetic traps, and wherein, in the on state, the local magnetic fields persist after the temporary magnetic field is discontinued.

2. The method of manipulating magnetic particles according to claim 1, wherein the plurality of magnetic particles are at least one of magnetically tagged biological species, magnetically tagged cells, magnetically tagged molecules, and magnetically tagged polymers.

3. The method of manipulating magnetic particles according to claim 1, wherein the array of spin valve magnetic traps are attached to a membrane that is supported by a substrate.

4. The method of manipulating magnetic particles according to claim 3, wherein each of the spin valve magnetic traps comprise a multilayered spin-valve structure having two discrete magnetic layers encased in a multiple layer structure that together can selectively have either parallel or anti-parallel magnetic moments when subjected to the magnetic field to produce in total a local magnetic field that is capable of attracting and restraining and subsequently releasing magnetic particles near the spin valve magnetic traps.

5. The method of manipulating magnetic particles according to claim 3, wherein the membrane is transparent.

6. The method of claim 3, wherein the membrane is at least partially free-standing so as to define opposite surfaces, wherein the plurality of spin valve magnetic traps are attached to one of the opposite surfaces of the membrane, and wherein the fluid having the magnetic particles dispersed therein is brought proximate the array of spin valve magnetic traps on the other of the opposite surfaces of the membrane so that the membrane provides a barrier between the fluid and the plurality of spin valve magnetic traps.

7. The method of manipulating magnetic particles according to claim 6, wherein the membrane is transparent.

8. The method of manipulating magnetic particles according to claim 1, wherein the coplanar layers of material that produce the local magnetic field comprises a high moment low remnant field material.

9. The method of manipulating particles according to claim 1, wherein the material that produces a local magnetic field and has a high moment low remnant field is a nickel-iron alloy.

10. The method of manipulating magnetic particles according to claim 1, wherein each of the spin valve magnetic traps comprise a multilayered spin-valve structure having two discrete magnetic layers encased in a multiple layer structure that together can selectively have either parallel or anti-parallel magnetic moments when subjected to the magnetic field to produce in total a local magnetic field that is capable of attracting and restraining and subsequently releasing magnetic particles near the spin valve magnetic traps.

11. The method of manipulating magnetic particles according to claim 1, wherein each of the spin valve magnetic traps are arranged in an array and are sized to attract and restrain individual cells, molecules, or polymers that are magnetically tagged.

12. The method of manipulating magnetic particles according to claim 1, further comprising selectively applying a second auxiliary magnetic field to one or more of the plurality of spin valve magnetic traps to cause at least one or more magnetic particles held by the local magnetic field to rotate or move.

13. The method of manipulating magnetic particles according to claim 1, further comprising selectively applying a second magnetic field to one or more of the plurality of spin valve magnetic traps to cause at least one or more magnetic particles held by the local magnetic fields to be placed under tension or torsion.

14. The method of manipulating magnetic particles according to claim 1, further comprising using a moving magnetic tipped probe to provide a second auxiliary field to move one or more of the magnetic particles to desired locations near the spin valve magnetic traps.

15. The method of manipulating magnetic particles according to claim 14, wherein the magnetic tipped probe comprises a magnetic force microscope cantilever.

16. The method of claim 1, wherein the plurality of spin valve magnetic traps each comprise a multilayered spin-valve structure having two discrete magnetic layers encased in a multiple layer structure that together can selectively have either parallel or anti-parallel magnetic moments when subjected to the magnetic field to produce in total the local magnetic fields near the individual spin valve magnetic traps that are capable of attracting and retaining and subsequently releasing the magnetic particles by the spin valve magnetic traps.

17. The method of claim 1, wherein the plurality of spin valve magnetic traps each comprise a multilayered spin-valve structure having the following sequence of layers: a layer of tantalum, a layer of nickel-iron alloy, a layer of cobalt, a layer of copper, a layer of cobalt, a layer of nickel-iron alloy, a layer of IrMn and a layer of tantalum, wherein the layers of the nickel-iron alloy can selectively have either parallel or anti-parallel magnetic moments when subjected to the magnetic field to produce in total the local magnetic fields near the individual spin valve magnetic traps that are capable of attracting and retaining and subsequently releasing the magnetic particles by the spin valve magnetic traps.

18. A method of manipulating magnetic particles, comprising the steps of:
providing a fluid having a plurality of magnetic particles dispersed therein;
providing a plurality of spin valve magnetic traps attached to a membrane, each of the plurality of spin valve magnetic traps being switchable between an on state and an off state when temporarily subjected to a magnetic field of sufficient strength to change the magnetization state of the spin valve trap, (a) the on state characterized in that the spin valve magnetic trap produces its own local magnetic field which persists after the temporary magnetic field is discontinued, said produced local magnetic field being capable of attracting and indefinitely retaining the magnetic particles proximate the spin valve magnetic trap, and (b) the off state characterized in that no local magnetic field is produced by the spin valve magnetic trap and the magnetic particles are not attracted or retained proximate the spin valve magnetic trap;
bringing the fluid having the magnetic particles dispersed therein proximate the array of spin valve magnetic traps; and
attracting and retaining the magnetic particles proximate one or more of the plurality of spin valve magnetic traps by temporarily subjecting the spin valve magnetic traps to the magnetic field so as to selectively switch one or more of the spin valve magnetic traps between the on and off states thereof.

19. The method of claim 18, wherein the plurality of spin valve magnetic traps are individually switchable between the on and off states thereof, and wherein the step of attracting and retaining magnetic particles proximate one or more of the plurality of spin valve magnetic traps comprises individually temporarily subjecting each spin valve magnetic trap to the magnetic field so as to selectively switch each spin valve magnetic trap between the on and off states thereof.

20. The method of claim 18, wherein the plurality of spin valve magnetic traps are globally switchable between the on and off states thereof, and wherein the step of attracting and retaining magnetic particles proximate one or more of the plurality of spin valve magnetic traps comprises globally temporarily subjecting the plurality of spin valve magnetic traps to the magnetic field so as to selectively switch all of the plurality of spin valve magnetic traps between the on and off states thereof.

21. The method of claim 18, wherein the plurality of spin valve magnetic traps are both individually and globally switchable between the on and off states thereof, and wherein the step of attracting and retaining magnetic particles proximate one or more of the plurality of spin valve magnetic traps comprises one of (a) individually temporarily subjecting each spin valve magnetic trap to the magnetic field so as to selectively switch each spin valve magnetic trap between the on and off states thereof, or (b) globally temporarily subjecting the plurality of spin valve magnetic traps to the magnetic field so as to selectively switch all of the plurality of spin valve magnetic traps between the on and off states thereof.

22. The method of claim 18, wherein the membrane is at least partially free-standing so as to define opposite surfaces, wherein the plurality of spin valve magnetic traps are attached to one of the opposite surfaces of the membrane, and wherein the fluid having the magnetic particles dispersed therein is brought proximate the array of spin valve magnetic traps on the other of the opposite surfaces of the membrane so that the membrane provides a barrier between the fluid and the plurality of spin valve magnetic traps.

23. The method of claim 18, wherein the plurality of spin valve magnetic traps each comprise a multilayered spin-valve structure having two discrete magnetic layers encased in a multiple layer structure that together can selectively have either parallel or anti-parallel magnetic moments when subjected to the magnetic field to produce in total the local magnetic fields near the individual spin valve magnetic traps that are capable of attracting and retaining and subsequently releasing the magnetic particles by the spin valve magnetic traps.

24. The method of claim 18, wherein the plurality of spin valve magnetic traps each comprise a multilayered spin-valve structure having the following sequence of layers: a layer of tantalum, a layer of nickel-iron alloy, a layer of cobalt, a layer of copper, a layer of cobalt, a layer of nickel-iron alloy, a layer of IrMn and a layer of tantalum, wherein the layers of the nickel-iron alloy can selectively have either parallel or anti-parallel magnetic moments when subjected to the magnetic field to produce in total the local magnetic fields near the individual spin valve magnetic traps that are capable of attracting and retaining and subsequently releasing the magnetic particles by the spin valve magnetic traps.

* * * * *